United States Patent [19]
LaPrairie

[11] Patent Number: 4,610,036
[45] Date of Patent: Sep. 9, 1986

[54] SUNGLASSES

[76] Inventor: Brian B. LaPrairie, 44 Mayfield St., Dover, Pa. 17315

[21] Appl. No.: 772,444

[22] Filed: Sep. 4, 1985

[51] Int. Cl.⁴ .............................................. A61F 9/04
[52] U.S. Cl. .......................................... 2/12; 2/450
[58] Field of Search .............. 2/12, 13, 15, 426, 438, 2/439, 442, 448, 449, 450, 451, 454; 206/472; 351/41, 46

[56] References Cited

U.S. PATENT DOCUMENTS

| | | |
|---|---|---|
| 1,319,639 | 10/1919 | Brubaker et al. |
| 1,562,319 | 11/1925 | Fairall |
| 2,426,266 | 8/1947 | Haas |
| 2,527,027 | 10/1950 | Mull .................................. 2/450 |
| 2,589,575 | 3/1952 | Richardson et al. ................. 2/454 |
| 2,975,426 | 3/1961 | Rabb .............................. 2/454 X |
| 3,023,418 | 3/1962 | Hammond .......................... 2/13 |
| 3,171,134 | 3/1965 | Kennedy ........................... 2/13 |
| 3,505,679 | 4/1970 | Bennett ............................ 2/13 |
| 3,526,449 | 9/1970 | Bolle et al. ........................ 351/41 |
| 4,012,129 | 3/1977 | Byler .............................. 351/46 |
| 4,262,367 | 4/1981 | Herrin ............................. 2/12 |
| 4,306,737 | 12/1981 | Errichiello .................... 206/472 X |
| 4,503,974 | 3/1985 | Lane ........................... 206/472 X |

Primary Examiner—Louis K. Rimrodt
Attorney, Agent, or Firm—Thomas Hooker

[57] ABSTRACT

A pair of plastic glasses including an injection molded one-piece integral lens and temple piece having a lens portion with two lenses and a narrow bridge, and a pair of temple portions at the ends of the lens portion. Vertical hourglass hinges join the temple and lens portions. These portions are formed of essentially uniform thickness optically clear plastic without knit lines. Two earpieces are adjustably mounted on the temple portions.

8 Claims, 7 Drawing Figures

U.S. Patent   Sep. 9, 1986   4,610,036
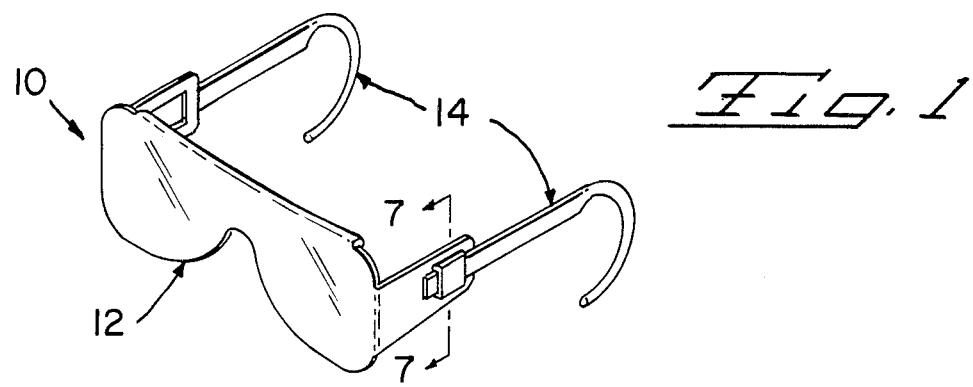
Fig. 1
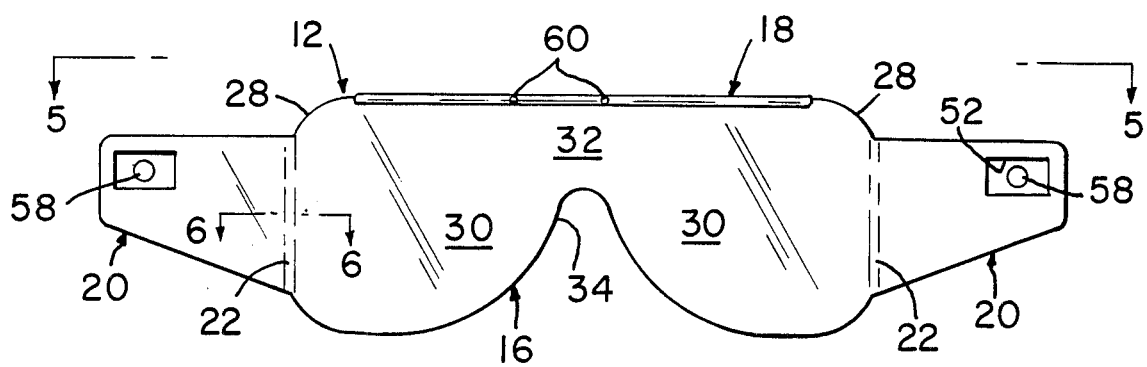
Fig. 2
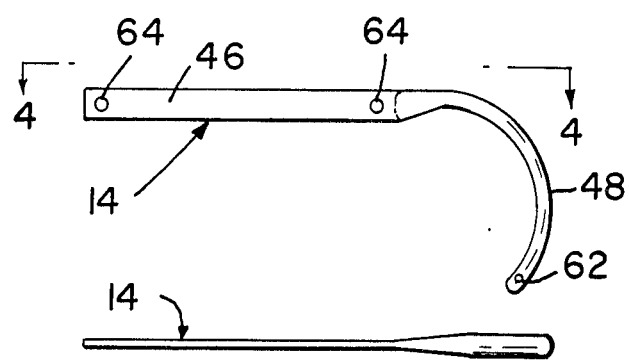
Fig. 3
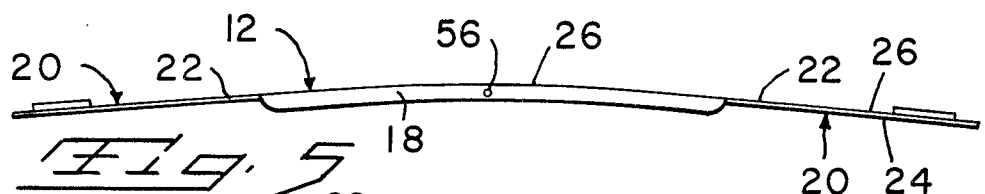
Fig. 4
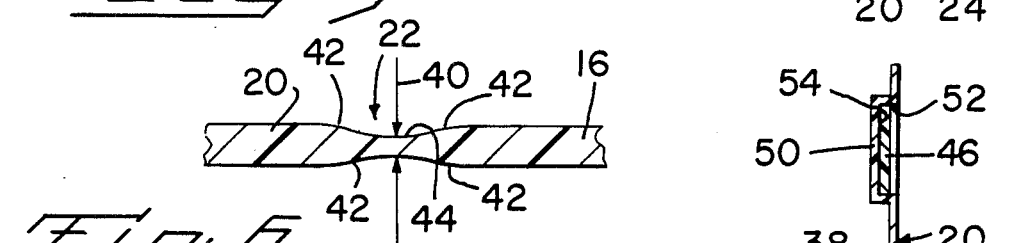
Fig. 5
Fig. 6
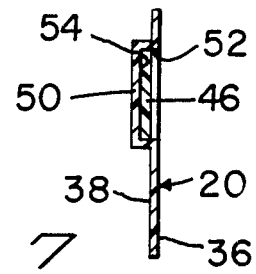
Fig. 7

SUNGLASSES

This invention relates to injection molded plastic sunglasses and glasses with optically smooth lenses and temple pieces, reliable hinges joining the lenses and temple pieces and plastic earpieces adjustably secured to the temple pieces.

The prior art teaches stamping integral glasses lens and temple pieces from uniform thickness stock material. The material is simply bent to form a hinge at the lens-temple piece junctions. See U.S. Pat. No. 2,527,027. The hinges of this design are very weak, therefore limiting the usefulness of the glasses. U.S. Pat. No. 3,721,490 discloses molded flat temple pieces which are attached to the ear pieces of conventional eyeglasses. This type of temple piece does not join the eyeglass lenses and does not provide a continuous shield surrounding the eyes from temple to temple.

The eyeglasses and glasses of the present invention are injection molded with continuous optically smooth lens and temple portions joined by specialized integral plastic hinges. The hinges allow repeated flexing of the temple portions relative to the lens portion without failure and also form part of the continuous protection provided by the glasses. A curved stiffening bar extends along the top of the lens portion of the glasses to stiffen the relatively thin lenses and more closely conform the lenses to the face of the wearer.

The lens and temple piece is injection molded using a single injection port in order to assure formation of optically smooth inner and outer surfaces without knit lines. The molds are provided with ejection pins which engage non-optical parts of the lens and temple piece so that the slight roughness formed in the piece over the injection pins does not impair the optical properties of the glasses. The earpieces of the glasses are adjustably fitted in channels located on the outside of the temple pieces. The slight roughness formed on the inside of the channels by the ejection pins aids in frictionally holding the earpieces in proper position.

Other objects and features of the invention will become apparent as the description proceeds, especially when taken in conjunction with the accompanying drawings illustrating the invention, of which there is one sheet and one embodiment.

In the Drawings:

FIG. 1 is a perspective view of a pair of sunglasses according to the invention;

FIG. 2 is a front view of the lens and temple piece as molded;

FIG. 3 is a side view of an earpiece used in the invention;

FIGS. 4 and 5 are top views taken respectively along line 4—4 of FIG. 3 and line 5—5 of FIG. 2;

FIG. 6 is a sectional view taken along line 6—6 of FIG. 2; and

FIG. 7 is a sectional view taken along line 7—7 of FIG. 1.

Sunglasses 10 include a unitary injection molded lens and temple piece 12 shown in FIGS. 2 and 5 and a pair of earpieces 14 shown in FIGS. 3 and 4. The lens and temple piece 12 is injection molded from propionate smoke tinted transparent molding resin and an ultraviolet light inhibitor. The piece 12 includes a lens portion 16, a stiffening bar 18 extending along the top of the lens portion and a pair of like temple portions 20 joined to the ends of the lens portion by straight, smooth hourglass hinges 22 as shown in FIG. 6. The inner and outer surfaces 24 and 26 of the lens and temple portions of piece 12 are parallel to each other and are optically smooth.

As shown in FIG. 5, bar 18 extends inwardly of the lens portion 16 past the inner lens portion surface 24 and is inwardly curved so that the lens portion is curved with the lens portion on the outside of the bar for an improved fit on the face of the wearer. The outer lens portion surface 26 is concave in horizontal section and straight in vertical section. The stiffening bar supports the lens portion against undesired flexing during use of the sunglasses and bending of the temple portions about hinges 22. As shown, the bar extends along the major width of the lens portion between the two smooth corners 28. The corners join the ends of the bar to the tops of the hinges 22. The light transmitting part of the lens portion 16 includes two large area viewing lenses 30 and a narrow bridge 32 joining the lenses. Bridge 32 is located between the bar and nose recess 34.

The temple portions 20 of the lens and temple piece 12 are integral with the lens portion 16 and include flat inner and outer parallel and optically smooth surfaces as described. The temple and lens portions 20 and 16 are preferably about 0.02 inch thick. The hinges 22 as shown in FIG. 6 have a smooth hourglass cross section with a minimum thickness at the center of the hourglass as indicated at reference number 40 less than the thickness of the joined lens and temple portions. The inner and outer surfaces of the hinges each include a smooth convex shoulder bend 42 extending from the adjacent surface of the lens or temple portion to a smooth central concave bend 44 adjacent the minimum thickness portion. The hinge 22 may have a minimum thickness of about 0.012 inch. The smooth, straight hourglass hinges as described provide a strong and reliable connection between the lens and temple portions permitting repeated flexing of the temple portions from the 90 degree position relative to the lens piece as shown in FIG. 1 to a collapsed position where the temple portions overlie the adjacent lenses 30. The strength of the smooth hourglass hinges prolongs the useful life of sunglasses 10. Hinges 22 may be flexed 40 to 50 or more times without cracking.

The earpieces 14 are injection molded from polypropylene plastic similar to the plastic used in molding the lens and temple piece 12. Each earpiece includes an elongate temple strip 46 and a curved earguard 48 at one end of strip 46. The temple portions 20 each include an integral molded strip channel 50 located in the temple portion away from hinge 22 and projecting outwardly of the outer surface 38. The channel 50 overlies an opening 52 in the temple piece. The channel and the outer surface of the temple piece define a slot 54 having a tight sliding fit with the earpiece temple strip 46 such that the strips may be inserted into the slots 54 as shown in FIG. 1. The tightness of the fit between the earpieces and temple portions permits the wearer to adjust the earpieces in or out as required for proper fit.

The lens and temple pieces 12 of eyeglasses 10 are formed from an injection molding operation using a pair of separable die halves which, when closed, define a cavity having the shape of the lens and temple piece. Plastic is flowed into this cavity through a single gate located at the center top of the bar 18 above the nose recess 34. The location of the injection port is indicated by reference number 56 in FIG. 5. Using the single port as described, the hot molten plastic is flowed through the port, along the bar which serves as a carrier and into the interior opening between the mold halves. The plastic fills the bar and flows to and through the symmetrical halves of the cavity to either side of the port in a single wave thereby forming the clear, optically smooth lens and temple piece. Injection molding of a lens and temple piece using plural mold ports would involve intersecting double wave flow of molten plastic into the mold cavity. The wave intersections result in visible knit lines. Such lines impair the optical characteristics of the plastic and are avoided by injection molding of the piece using a single port. Location of the port on the bar 18 assures that the roughness inhered in breaking the bar away from the plastic retained in the port does not impair the optical properties of the lens and temple piece.

A number of ejection pins are provided in one mold half for removing the molded piece from the open mold half. The pins are located to contact surfaces 58 on the inside of the channels 50 and surfaces 60 on the edge of bar 18 away from the lens portion of piece 12 and adjacent the nose recess. The ejection pins cause a slight roughness on the surface of the molded part. The roughness on the lens and temple piece caused by the ejection pins does not affect the smooth parallel optical surfaces of the major portions of the lens and temple portions. The roughness 58 on the inner surface of channel 50 frictionally engages the temple strip to aid in holding the earpieces in proper position on the temple pieces.

The earpieces are molded similarly to the lens and temple piece 12 using the single injection port located at 62. Ejection pins remove the earpiece from an open mold half and contact surfaces 64 on the ends of the strip 46. The surfaces 64, like surfaces 58 and 60, are rough and do not add to the attractive appearance of sunglasses 10. The surfaces may be concealed from view by positioning the earpieces on the temple portions with the surfaces 64 facing inwardly against the outer temple piece surfaces 26.

Sunglasses 10 reduce visual and ultraviolet light thereby protecting the wearer's eyes, both from light directed from the front and also light directed from the sides. This protection is particularly important in preventing injury to the eyes during the post-mydriatic period or for protection of aphakic eyes. The degree of protection afforded by the sunglasses may be varied by varying the proportion of ultraviolet inhibitor added to the plastic and strength of the smoke tint within the plastic as required.

While the invention has been described in connection with sunglasses, clear glasses of the type described may be molded from clear transparent plastic. For instance, transparent glasses of the type described may be used as disposable safety glasses in shops or other work areas where there is a risk of eye injury.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A pair of plastic glasses including a one-piece injection molded plastic lens and temple piece having an elongate lens portion, a pair of temple portions at the ends of the lens portion and a pair of straight hourglass hinges extending transversely of the lens and temple piece and joining the temple portions to the lens portion, the lens portion having a narrow central bridge and a pair of wide viewing lenses located between the bridge and the hinges, and a stiffening bar extending along the top of the viewing lenses and bridge, each temple portion extending a distance away from the adjacent hinge, said viewing lenses, bridge and temple portions all being formed from essentially uniform thickness light transmitting and optically clear plastic free of knit lines extending, with the exception of the stiffening bar, continuously from the top to the bottom of the lens and temple piece and, with the exception of the hinges, from the end of one temple portion across the lens portion to the end of the opposite temple portion, whereby the lens and temple piece is light transmitting through optically clear surfaces and forms a continuing shield surrounding the eyes from temple to temple; and a pair of earpieces adjustably mounted to the temple portions at locations away from the hinges.

2. Glasses as in claim 1 wherein the hinges each include two smooth concave shoulder bends and a smooth convex central bend joining the shoulder bends on each side of the hinge, the hinges having a minimum thickness at the central bends.

3. Glasses as in claim 2 wherein lens the minimum thickness of the hinges is about 3/5th the thickness of the optically clear plastic.

4. Glasses as in claim 1 including the lens portion includes a pair of spaced lenses, a bridge joining the lenses above a nose recess and a single central injection port contact area located on the bar above the bridge.

5. Glasses as in claim 1 including integral channels formed on the outsides of the temple pieces and defining strip receiving slots having inner surfaces, such surfaces including roughened ejection pin contact areas, and the earpieces each including strips having frictional fits within the slots, such strips being fitted within the slots and including friction connections securing the strips to the contact areas.

6. Glasses as in claim 5 including injection pin contact areas on the bar to either side of the bridge.

7. Glasses as in claim 1 wherein the lens and temple piece is formed of uniformly tinted plastic material including an ultraviolet light inhibitor.

8. Glasses as in claim 1 wherein said lens and temple piece is formed of transparent plastic.

* * * * *